(12) United States Patent
Nakamura et al.

(10) Patent No.: US 7,052,490 B2
(45) Date of Patent: May 30, 2006

(54) CORNEAL SURGERY APPARATUS AND CORRECTION DATA DETERMINING METHODS

(75) Inventors: Takua Nakamura, Hoi-gun (JP); Yoshitaka Suzuki, Okazaki (JP); Motohiro Sugiura, Gamagori (JP)

(73) Assignee: Nidek Co., Ltd. (JP)

( * ) Notice: Subject to any disclaimer, the term of this patent is extended or adjusted under 35 U.S.C. 154(b) by 0 days.

(21) Appl. No.: 09/964,449

(22) Filed: Sep. 28, 2001

(65) Prior Publication Data

US 2002/0040219 A1   Apr. 4, 2002

(30) Foreign Application Priority Data

Sep. 29, 2000   (JP)   ............... 2000-302863

(51) Int. Cl.
    *A61B 18/18*   (2006.01)
(52) U.S. Cl. ............... 606/5; 606/4; 351/212
(58) Field of Classification Search ........ 606/4–6, 606/10–12; 351/200, 211, 212, 219, 161; 128/898
See application file for complete search history.

(56) References Cited

U.S. PATENT DOCUMENTS

| | | | |
|---|---|---|---|
| 5,173,723 A * | 12/1992 | Volk | 156/234 |
| 5,395,356 A | 3/1995 | King et al. | 606/4 |
| 5,445,633 A | 8/1995 | Nakamura et al. | 606/5 |
| 5,507,799 A | 4/1996 | Sumiya | 606/5 |
| 5,556,395 A | 9/1996 | Shimmick et al. | 606/4 |
| 5,562,656 A | 10/1996 | Sumiya | 606/4 |
| 5,637,109 A | 6/1997 | Sumiya | 606/5 |
| 5,691,797 A * | 11/1997 | Seidner et al. | 351/161 |
| 5,713,892 A | 2/1998 | Shimmick | 606/5 |
| 5,777,719 A * | 7/1998 | Williams et al. | 351/212 |
| 5,786,883 A * | 7/1998 | Miller et al. | 351/162 |
| 5,800,424 A | 9/1998 | Sumiya | 606/4 |
| 5,906,608 A | 5/1999 | Sumiya et al. | 606/5 |
| 6,190,374 B1 * | 2/2001 | Amano et al. | 606/5 |
| 6,203,539 B1 | 3/2001 | Shimmick et al. | 606/5 |
| 6,280,435 B1 | 8/2001 | Odrich et al. | 606/5 |
| 6,296,867 B1 * | 10/2001 | Peyman | 424/429 |
| 6,364,483 B1 * | 4/2002 | Grossinger et al. | 351/161 |
| 6,416,179 B1 * | 7/2002 | Lieberman et al. | 351/212 |
| 6,436,092 B1 * | 8/2002 | Peyman | 606/5 |
| 6,592,574 B1 * | 7/2003 | Shimmick et al. | 606/4 |
| 6,685,320 B1 * | 2/2004 | Hirohara et al. | 351/221 |
| 6,802,605 B1 * | 10/2004 | Cox et al. | 351/160 R |
| 6,808,265 B1 * | 10/2004 | Cox | 351/219 |

\* cited by examiner

*Primary Examiner*—A. Farah
(74) *Attorney, Agent, or Firm*—Rader, Fishman & Grauer PLLC

(57) ABSTRACT

A corneal surgery apparatus for correcting a refractive error by ablating corneal tissue with a laser beam, being capable of finding a correction pattern optimum for a patient to ensure precise correction, and a method of determining correction data. The apparatus includes units for inputting refractive power data on a trial contact lens, converting the refractive power data to obtain ablation data, controlling an ablation amount of the corneal tissue based on the ablation data, storing the refractive power data corresponding to each contact lens, and revising the refractive power data. The method includes processes for obtaining a correction value made with a contact lens based on of an ophthalmic examination, selecting a contact lens based on the value and converting the refractive power data on the selected contact lens into the ablation data for correcting the refractive error if the trial use of the contact lens results favorably.

2 Claims, 7 Drawing Sheets

CORNEAL SURGERY APPARATUS AND CORRECTION DATA DETERMINING METHODS

BACKGROUND OF THE INVENTION

1. Field of the Invention

The present invention relates to a corneal surgery apparatus for correcting a refractive error by ablating corneal tissue with a laser beam and methods of determining data concerning the correction.

2. Description of Related Art

Refractive errors of an eye include myopia, astigmatism, hyperopia, and presbyopia which makes it difficult to see things from near with aging. Conventionally, correction of presbyopia has been conducted with eyeglasses, but contact lenses have also been used in recent years. On the other hand, refractive corrections of myopia, astigmatism and hyperopia have been conducted with a corneal surgery apparatus for changing a corneal shape with a laser beam as well as with eyeglasses and contact lenses. In the correction of presbyopia, however, patterns of the correction vary in accordance with patients' life styles. In corrective surgery with a laser beam, this variance makes it difficult to correct presbyopia according to an optimum pattern of correction desired by a patient. In addition, corrective surgery using a laser beam has a problem in that it is irreversible unlike the correction with eyeglasses or contact lenses.

SUMMARY OF THE INVENTION

The present invention has been made in view of the above circumstances and has an object to overcome the above problems and to provide: 1) a corneal surgery apparatus capable of finding an optimum pattern of correction desired by a patient so as to ensure precise correction and 2) a method of determining data concerning the correction. In particular, the invention is to provide a corneal surgery apparatus which may be applied to presbyopic correction and methods of determining optimum correction data for correcting presbyopia with the corneal surgery apparatus.

To achieve the objects and in accordance with the purpose of the present invention, as embodied and broadly described herein, a corneal surgery apparatus for correcting a refractive error by ablating corneal tissue with a laser beam comprises: input means for inputting refractive power data on a contact lens used on a trial basis; calculation means for converting the inputted refractive power data to obtain ablation data; and control means for controlling an ablation amount of the corneal tissue based on the obtained ablation data.

In another aspect of the present invention, a correction data determining method of correcting a refractive error by ablating corneal tissue comprises: a process in which a value of correction to be made with a contact lens is obtained based on a result of an ophthalmic examination; a process in which a contact lens for trial use is selected based on the obtained value of correction; and a process in which refractive power data on the selected contact lens is converted into ablation data for correcting the refractive error if the trial use of the contact lens bears a good result.

Further, in another aspect of the present invention, a corneal surgery apparatus for correcting a refractive error by ablating corneal tissue with a laser beam comprises: an ablation unit which comprises a laser light source emitting a laser beam and an irradiation optical system for irradiating the emitted laser beam onto a cornea; an input unit which inputs refractive power data on a contact lens used on a trial basis; a calculation unit which converts the inputted refractive power data to obtain ablation data; and a control unit which controls the ablation unit based on the obtained ablation data.

Additional objects and advantages of the invention are set forth in the following description, are obvious from the description, or may be learned by practicing the invention. The objects and advantages of the invention may be realized and attained by means of instrumentalities and combinations particularly pointed out in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

The following detailed description of preferred embodiments consistent with the present invention will now be given referring to the accompanying drawings.

Figure 1:
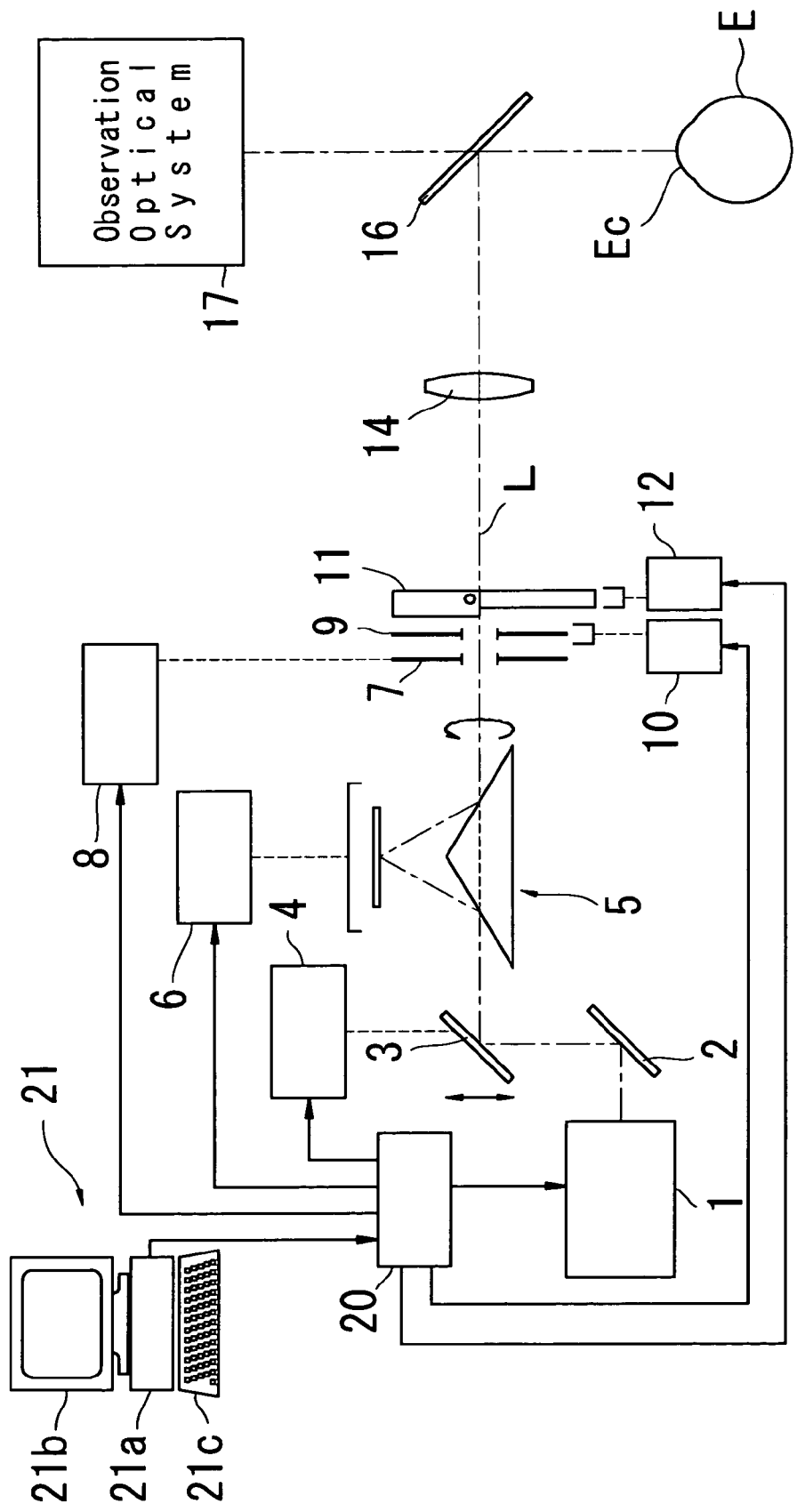
FIG. 1 is a view showing a schematic configuration of an optical system and a control system of a corneal surgery apparatus as one preferred embodiment according to the present invention.

FIG. 1 is a view showing a schematic configuration of an optical system and a control system in a corneal surgery apparatus as one of the preferred embodiments.

Figure 2:
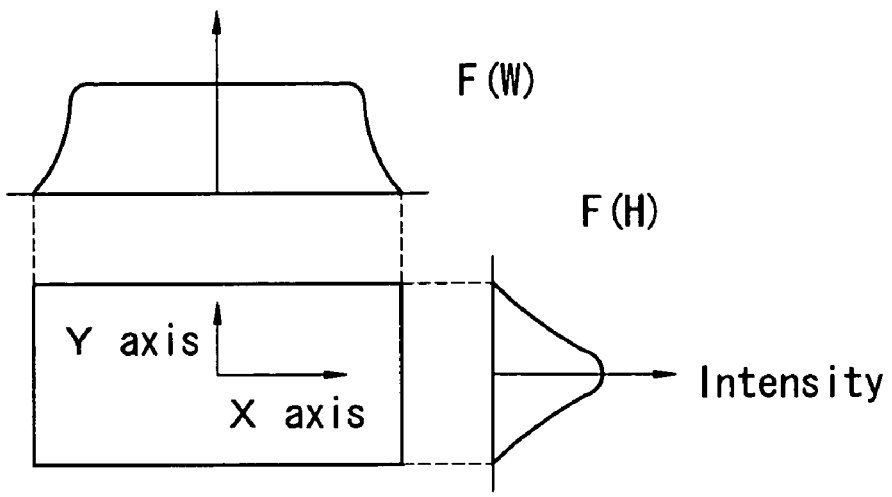
FIG. 2 is a view showing intensity distribution of an excimer laser beam applied to the corneal surgery apparatus shown in FIG. 1.

A laser light source 1 emits a laser beam, and in the present embodiment, a laser light source which emits an excimer laser beam with a wavelength of 193 nm (preferably within 200 nm) may be used. The excimer laser beam emitted from the laser light source 1 is a pulse wave. Typically, the wave takes a shape of top hat distribution F(W) in which intensity distribution of a beam is approximately uniform in the horizontal direction (the direction of the X axis), and it takes a shape of the Gaussian distribution F(H) in the vertical direction (the direction of the Y axis)(see FIG. 2).

The laser beam emitted from the laser light source 1 is deflected 90 degrees by a plane mirror 2, and is then deflected again 90 degrees by a plane mirror 3. The mirror 3 may be moved by a driving unit 4 in the vertical direction (the direction of the arrow) so as to shift the laser beam parallel to the direction of the Gaussian distribution. This enables the laser beam to be displaced from an optical axis L of a beam directing optical system so as to ablate a subject evenly. For detailed description on this process, reference should be made to U.S. Pat. No. 5,507,799 (Japanese Patent Unexamined Publication No. HEI 04-242644).

An image rotator 5 is rotationally driven on the optical axis L by a driving unit 6 so as to rotate the laser beam around the optical axis L.

A changeable circular aperture 7 restricts an ablation zone to a circular shape, and an opening region of the aperture 7 is changed in size (in diameter) by a driving unit 8. A changeable slit aperture 9 restricts an ablation zone to a slit shape. The slit aperture 9 is changed in width and is rotated on the optical axis L by a driving unit 10. The slit aperture 9 is used when correcting astigmatism.

Figure 3A:
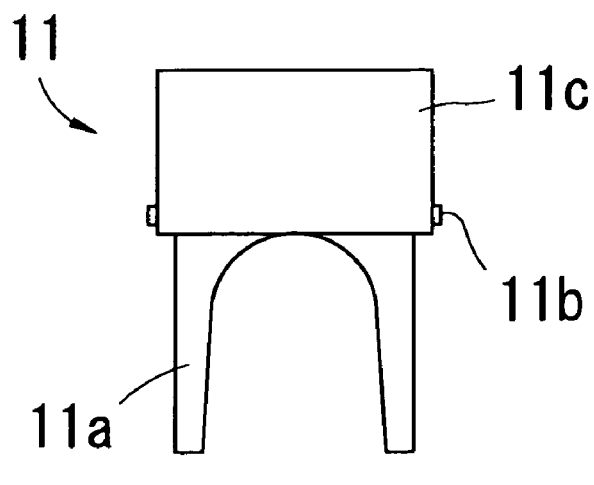
FIGS. 3A and 3B are views showing a schematic configuration of a beam restricting unit used in the corneal surgery apparatus shown in FIG. 1.
Figure 3B:
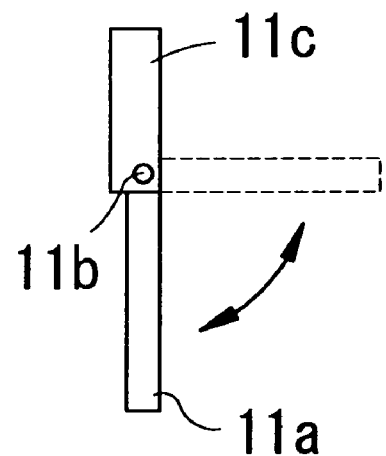

A beam restricting unit 11 has an aperture 11*a* of an approximately semi-oval shape. FIG. 3A is a view of the restricting unit 11 as viewed from the direction of the optical axis L, and FIG. 3B is a side elevation view of the unit 11. The aperture 11*a* rotates 90 degrees about an axis 11*b*. When the aperture 11*a* is positioned in broken lines as shown in FIG. 3B, the laser beam is transmitted except as obstructed by a shielding plate 11*c*. On the other hand, while the aperture 11*a* is rotating to a position indicated in solid lines, the laser beam is restricted by the shape of the aperture 11*a*. The restricting unit 11 is used when correcting presbyopia; otherwise it is removed from an optical path. A driving unit 12 comprises a driving part for inserting/removing the restricting unit 11 in/from the optical path and for rotating the aperture 11*a* and rotating a whole part of the restricting unit 11 about the optical axis L.

A projecting lens 14 projects the circular aperture 7 and the slit aperture 9 on a cornea Ec of a patient's eye E. A dichroic mirror 16 has a property of reflecting the excimer laser beam of 193 nm and transmitting the visible light. The beam passed through the lens 14 is reflected by the dichroic mirror 16, and is then deflected 90 degrees to be directed to the cornea Ec.

An observation optical system 17 has a binocular surgical microscope. Description as to the binocular observation optical system will be omitted since it is commercially available and its configuration is not related to the present invention.

In surgery, the eye E is aligned to be brought into a predetermined positional relationship with the apparatus. In addition, the eye E is maintained in the aligned state by looking at an unillustrated fixation target. The alignment is performed by projecting slit images onto the eye E from at least two directions between which the optical axis of the observation optical system (an unillustrated objective lens) is positioned, and positioning is then conducted based on positional relationships between or among the slit images. This process is described in detail in U.S. Pat. No. 5,562,656 (Japanese Patent Unexamined Publication No. HEI 06-47001,) which may be referred to.

A computer 21 receives input of refractive power data and the like concerning the patient's eye E to obtain control data for the apparatus. The computer 21 comprises a main body 21*a* of the computer with a program for obtaining ablation data and a database, a monitor 21*b* on which an input screen and inputted information are displayed, and an input control part 21*c* consisting of a keyboard and a mouse. The control data obtained by the computer 21 are inputted to a control device 20 which controls operations of the laser light source 1 and each of the driving units.

Brief description will now be given to ablation methods for correcting myopia, hyperopia and astigmatism in the above configurations.

Figure 4:
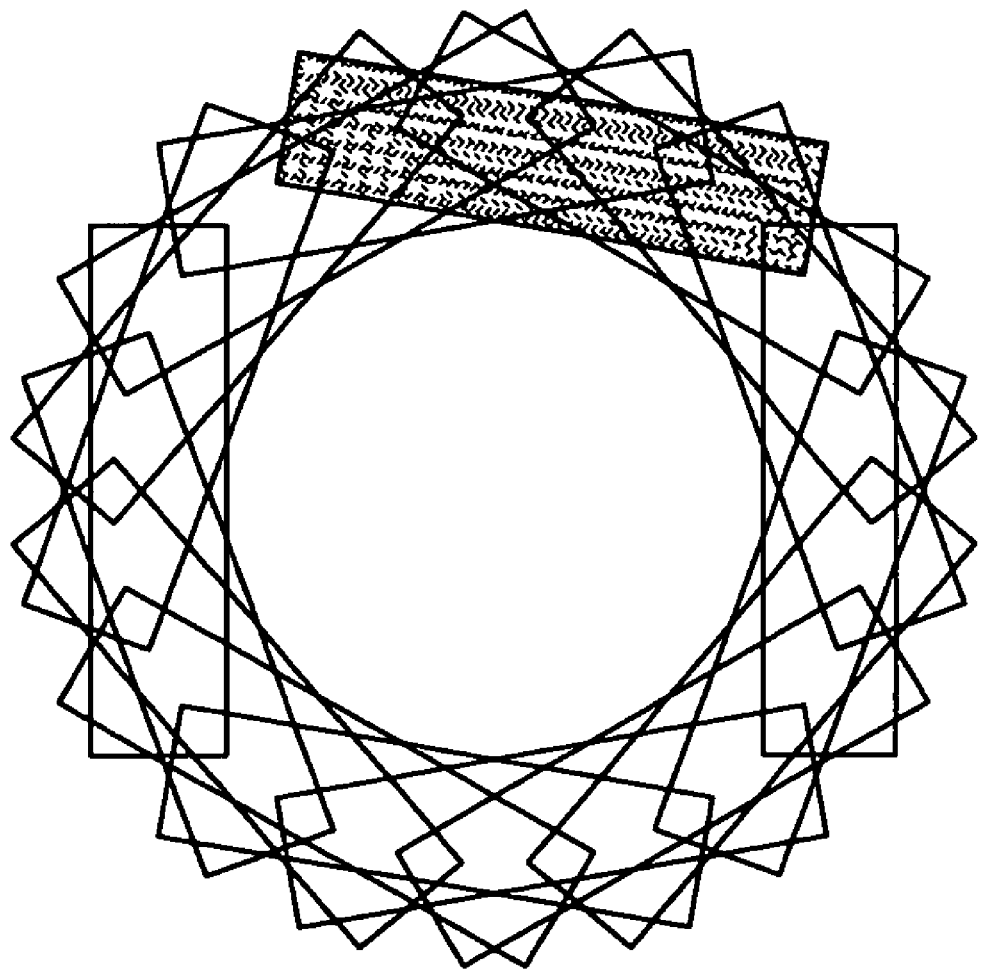
FIG. 4 shows an ablation pattern in an annular shape made by beams overlapping one another.

For hyperopic correction, the opening region (diameter) of the circular aperture 7 is fixed to restrict an ablation zone. The mirror 3 is displaced from the optical axis L to deviate the laser beam, and the image rotator 5 is rotated to shift the deviated laser beam so as to interlock a chain of ablated spots. The pattern formed by interlocking the ablated spots may be put into a nearly annular shape, as shown in FIG. 4, by selecting an appropriate combination of a rotational frequency of the image rotator 5 and a pulse repetition frequency of the laser pulse. The number of irradiation pulses (irradiation time) is increased as a deviation of the laser beam from the optical axis L is increased by sequential movements of the mirror 3. This allows hyperopia to be corrected in such a manner that a central portion of a cornea is ablated in lesser depth, and that a peripheral portion of the cornea ablated is in greater depth. Diopters are controlled by changing a total number of irradiation pulses, but without making any change in a ratio of the number of irradiation pulses for one position to that for another position of the laser beam deviated from the optical axis L by the movements of the mirror 3. For more details on this process, reference should be made to U.S. Pat. No. 5,800,424 (Japanese Patent Unexamined Publication HEI 08-66420).

Myopia may be corrected by two different methods. The first method for myopic correction is as follows: the circular aperture 7 restricts an ablation zone, the mirror 3 is sequentially moved to shift the laser beam in the direction of the Gaussian distribution, and the image rotator 5 rotates the direction in which the laser beam is shifted each time the laser beam completes one zone by moving from one end to the other end of the opening region of the circular aperture 7, thereby carrying out ablation in a uniformly circular shape as a whole. These operations are repeated while the opening region (diameter) of the circular aperture 7 is varied stepwise. This enables ablation to be carried out in the greatest depth on the corneal center, and in the lesser depth on the corneal periphery. For more details on this process, U.S. Pat. No. 5,637,109 (Japanese Patent Unexamined Publication No. HEI 06-114083) is to be referred.

The second method for myopic correction is a method to which the ablation for hyperopic correction is applied. By this method, a laser beam is rotated in the neighborhood of the corneal center such that ablation is carried out in greater depth on the corneal center, and in lesser depth on the corneal periphery. Accordingly, myopia may be corrected by carrying out ablation while the position of the laser beam deviated by the movements of the mirror 3 and the number of irradiation pulses are being controlled. As in the case of hyperopic correction, diopters may be controlled by changing the number of irradiation pulses at each position of the laser beam.

Astigmatism may be corrected by enlarging the opening region (width) of the slit aperture 9 while the laser beam is shifted to carry out ablation as is the case with the first method for myopia correction.

Next, description will now be given to typical patterns of presbyopic correction profile and their corresponding methods of ablation. The description will be based on an assumption that myopic eyes are to be corrected.

FIGS. 5A to 5E illustrate first and second patterns of presbyopic correction. The first pattern of presbyopic correction is a correction pattern in which a central correction zone 50 with its center positioned at a pupil and a peripheral correction zone 51 are used for near vision (eyesight from a short distance) and far vision (eyesight from a long distance), respectively. On an outer circumference of the zone 51, an unillustrated transition zone (TZ) is formed which smoothly connects an ablation zone and a non-ablation zone. The zone ranging from the pupil center to the zone 51 is an optical zone (OZ) which is optically influential.

In this pattern, the zone 50 for near vision is corrected by an amount of additional diopters in relation to the zone 51 for far vision. The method for this case varies depending on whether a value of myopic correction diopters S plus additional diopters ADD is negative or positive. In the case of S+ADD=0D, the zone 50 is ablated uniformly not to have any influence on refractive power (not to make any change in shape).

When the value of myopic correction diopters S plus additional diopters ADD is negative, for example, with the myopic correction diopters S=−3D and ADD=2D, the opening region (diameter)of the circular aperture 7 is controlled to ablate the zone 50 to correct myopia by a remaining amount of the myopic correction diopters S=−1D. Subsequently, while the opening region (diameter) of the circular aperture 7, which has become as large as the size of the zone 50, is gradually widened, the zone 51 is ablated to correct myopia by an amount of the myopic correction diopters S=−3D (see FIG. 5B).

When the value of myopic correction diopters S plus additional diopters ADD is positive, for example, with the myopic correction diopters S=−1D and ADD=2D, the zone 50 is corrected by the amount of S=+1D. In this case, while the zone 50 is ablated to correct hyperopia by an amount of S=+1D, the zone 51 is also ablated to correct myopia by the amount of the myopic correction diopters S=−1D using the second method for myopic correction to which the ablation for hyperopic correction is applied (see FIG. 5C).

Figure 5E:
FIGS. 5A to 5E illustrate first and second patterns of presbyopic correction.
Figure 5D:
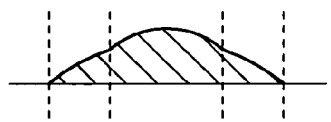
Figure 5C:
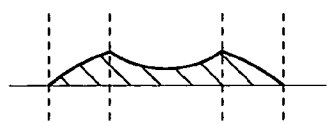
Figure 5B:
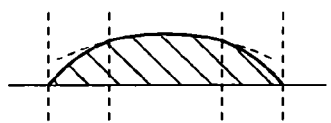
Figure 5A:
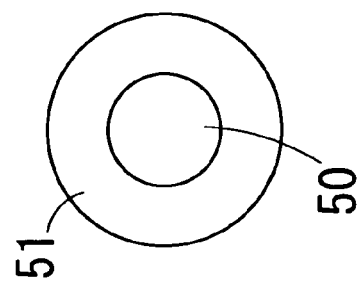

The second pattern of presbyopic correction is reverse to the first pattern of presbyopic correction; it is a correction pattern in which the zones 50 and 51 shown in FIG. 5A are used for far vision and near vision, respectively. In the second pattern of presbyopic correction, the method also varies depending on whether the value of myopic correction diopters S plus additional diopters ADD is negative or positive. In the case of S+ADD=0D, the zone 51 is not ablated, or is ablated uniformly.

When the value of myopic correction diopters S plus additional diopters ADD is negative, for example, in the case of the myopic correction diopters S=−3D and ADD=2D, the opening region (diameter) of the circular aperture 7 is controlled to ablate the zone 50 to correct myopia by the amount of the myopic correction diopters S=−3D, and then the zone 51 is also ablated to correct myopia by the remaining amount of the myopic correction diopters S=−1D (see FIG. 5D).

When the value of myopic correction diopters S plus additional diopters ADD is positive, for example, in the case of the myopic correction diopters S=−1D and ADD=2D, the zone 50 is ablated to correct myopia by the amount of S=−1D. Thereafter, the zone 51 is ablated to correct hyperopia by the amount of S=+1D (see FIG. 5E).

Incidentally, in any case of the above patterns, it may be preferred that a graduated zone having a continuously varying dioptric power should be provided between the zones 50 and 51. This may be achieved during a transition from the zone 50 to the zone 51 in such a manner that diopters are changed by carrying out ablation to correct myopia under the method by which the opening region (diameter) of circular aperture 7 is controlled or under the second method for myopic correction.

Figures 6A, 6B:
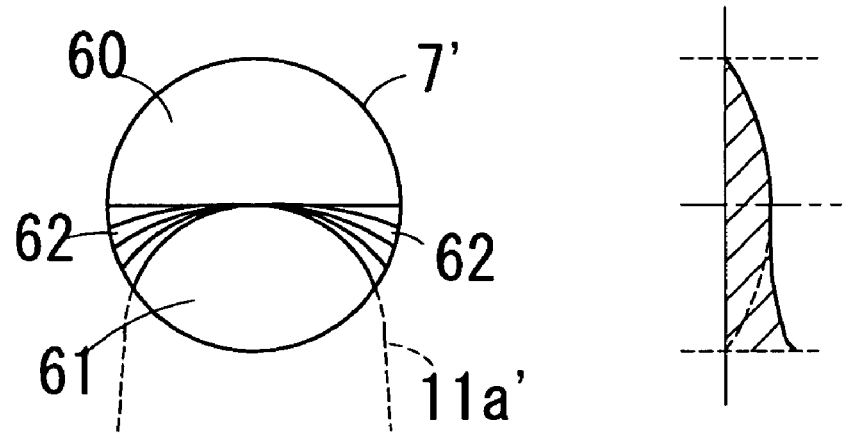
FIGS. 6A and 6B illustrate a third pattern of presbyopic correction.

FIGS. 6A and 6B illustrates a third pattern of presbyopic correction. In this pattern, as shown in FIG. 6A, an upper correction zone 60 in a semicircular shape is used for far vision, and a lower correction zone 61 which is a section enclosed by a circle 7' and a semicircle 11a' is used for near vision. A zone 62 is a transition zone smoothly connecting the zones 60 and 61.

Figure 7:
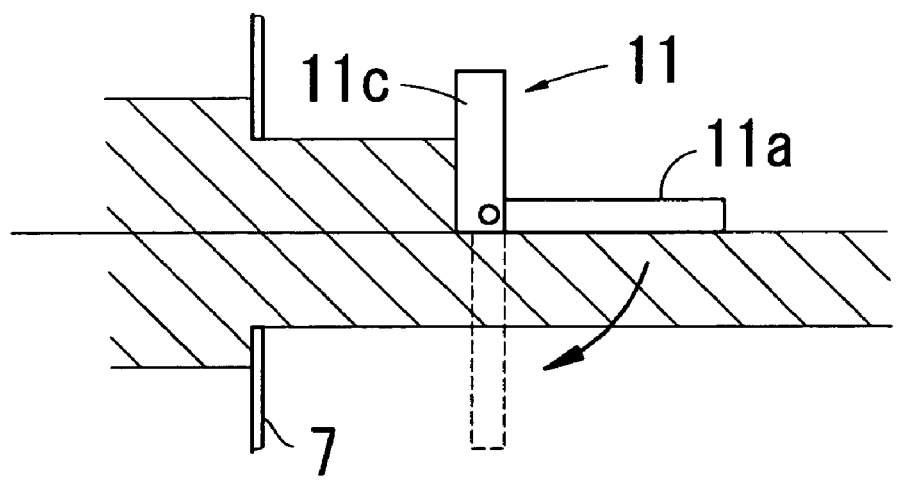
FIG. 7 illustrates an ablation method in the third pattern of presbyopic correction with the beam restricting unit.

In the third pattern, to begin with, the opening region (diameter) of the circular aperture 7 is controlled to ablate the inside of the optical zone including the zones 60 and 61 so as to correct myopia by an amount of myopic correction diopters for far vision. After that, the zone 61 is ablated in the following manner: the restricting unit 11 is inserted into the optical path so as to arrange the shielding plate 11c to shield the zone 60 as shown in FIG. 7; ablation is carried out to correct hyperopia by an amount of additional diopters with the opening region (diameter) of the circular aperture 7 kept in the same size as the optical zone, while the aperture 11a is gradually tilted from a position parallel to the optical axis until the aperture 11a becomes perpendicular to the optical axis; and this leads to ablate the zone 61 which is the section enclosed by the circle 7' (a passage zone of the circular aperture 7) and the semicircle 11a' (a passage zone of the aperture 11a) by an amount of the additional diopters (see FIG. 6B). During this ablation, tilting the aperture 11a gradually forms the zone 62.

The third pattern of presbyopic correction may be modified in various forms. For example, reversing a vertical relationship between positions of the zones 60 and 61 may make it possible to use the upper and the lower zones for near and far vision correction, respectively. This may be achieved by rotating the restricting unit 11 about the optical axis L. In addition, placement of both the zones may be changed without restraint; it does not have to be vertical, and may be horizontal where appropriate. Further, both the zones 60 and 61 may be changed in size by moving the restricting unit 11 and thereby shifting a position to place the aperture 11a.

As described above, the typical patterns of presbyopic correction have been disclosed, and it may be possible to follow a pattern of trifocal correction or to make a correction in a combination of some of the patterns mentioned above.

Additionally, the beam directing optical system for directing a laser beam to a patient's eye is not limited to the one disclosed in the present embodiment and its mode may come in various types. As described in U.S. Pat. No. 5,906,608 (Japanese Patent Unexamined Publication No. HEI 09-266925), for instance, it may be possible to employ a mode in which the laser beam shaped like a rectangle is split with a mask for selectively dividing a longitudinal direction of the beam, so that a position to project the beam onto a cornea may be shifted by the movement of the mirror 3 and the rotation of the image rotator 5. Alternatively, it may be also possible to employ a mode in which a galvano-mirror or the like is used for a two-dimensional scanning with a small-spot beam shaped within 1 mm, so that a position to project the small-spot beam may be shifted. With a beam directing optical system in these modes, ablation may be carried out in an arbitrary pattern of shape by controlling the irradiation time at each position of the beam.

Figure 8:
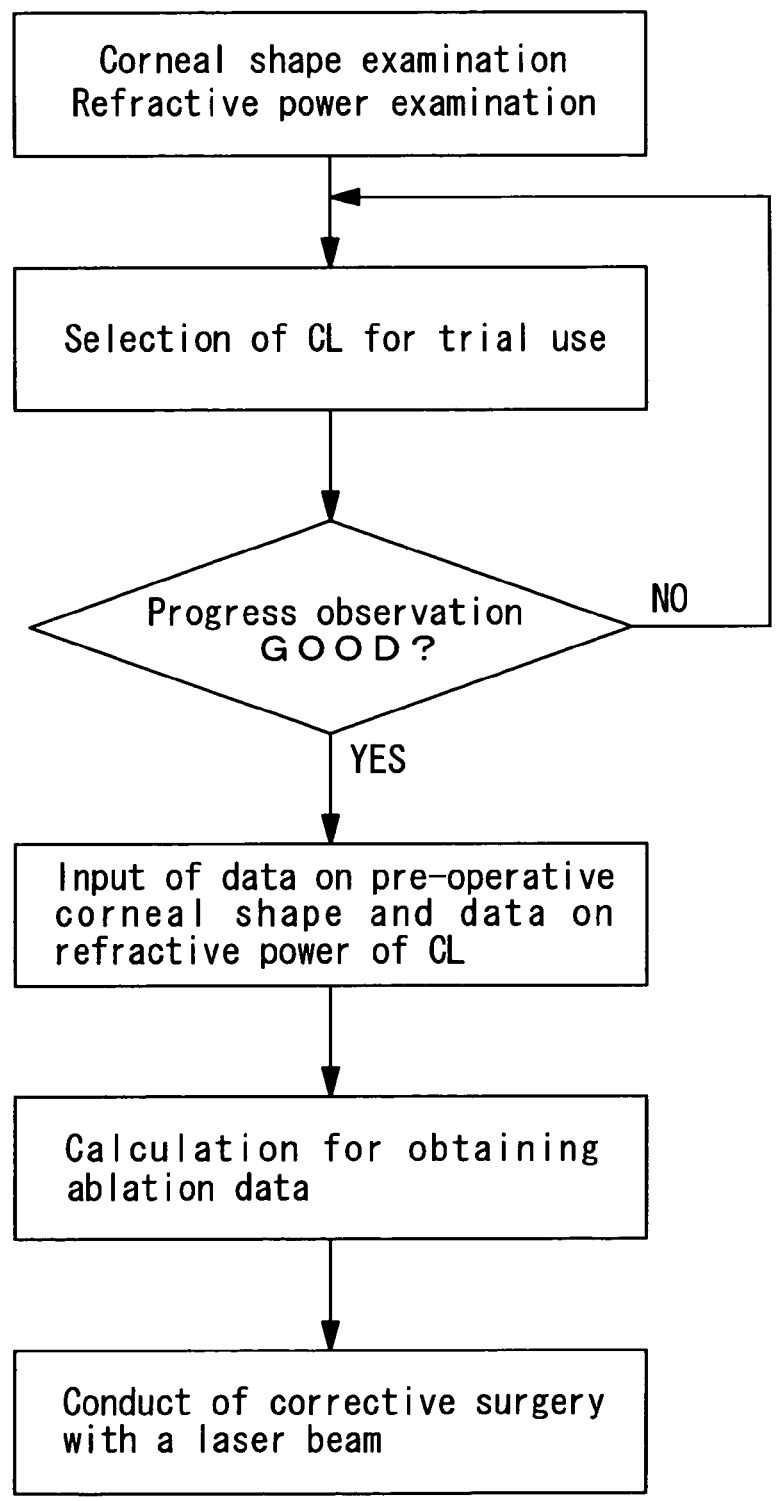
FIG. 8 is a flow chart depicting steps to correct presbyopia.

Next, steps to correct presbyopia with the present apparatus will now be described with reference to FIG. 8.

First, an ophthalmic examination such as a basic examination of corneal shapes or refractive powers is conducted to obtain a prescription of diopters for far and near vision corrections. Conventionally, refractive power data are determined at this stage and surgery is then performed. According to the present embodiment, however, prior to a keratorefractive surgery (corrective surgery) using a laser beam, a soft contact lens (hereinafter, referred to as CL) is used as a trial lens to confirm optimum correction pattern and corrective diopters. Based on a result thus confirmed, corrective surgery is then performed with a laser beam.

In advance of putting a CL on the eye E for trial use, it is required to prepare many different types of CLs that have their own correction profiles created in association with the correction patterns available with the above-stated corneal surgery apparatus. Manufacture of CLs may be conducted by a CL maker, based on data about the correction patterns stored in the apparatus, or it may also be possible to irradiate a beam on a CL having no dioptric power so that the CL may change in shape.

After the basic ophthalmic examination, an operator checks up on a patient's background of eyesight and life style, and selects a correction pattern, corrective diopters and the like for the patient. The operator makes the patient wear the selected CL on a trial basis, and observes a progress of any improvements achieved with the CL in the patient's vision for a while. For example, in the above-mentioned first to third patterns of presbyopic correction, the operator gives a test on different CLs with their far and near vision zones varied in size, from which he determines an optimum CL. He also confirms an optimum selection of corrective diopters for far vision and near vision each by making a test on several CLs. This process may put a patient through a simulation of the improvements in his vision that will be achieved through corneal surgery using a laser beam.

Figure 9:
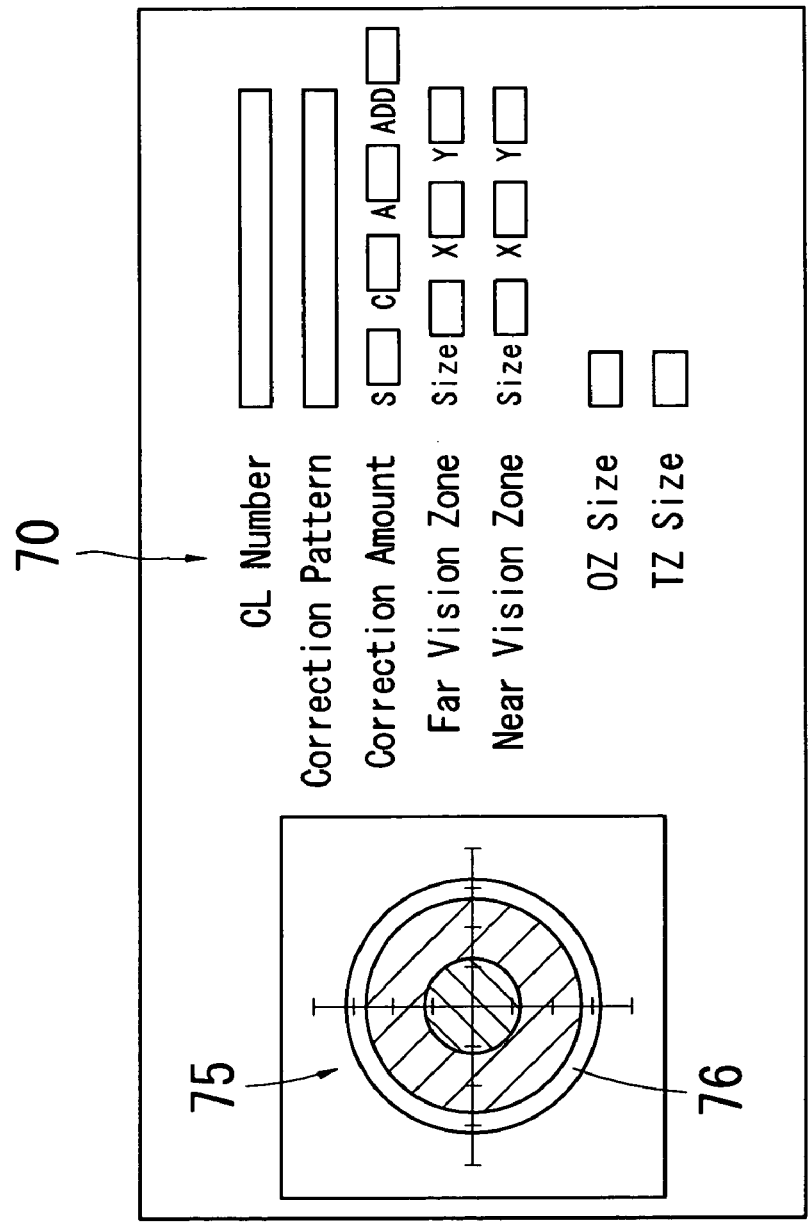
FIG. 9 is a view showing an example of a screen for input of refractive power data appearing on a display of the corneal surgery apparatus.

After the optimums for the patient is determined based on the progress observation, the computer 21 of the apparatus may receive an input of pre-operative corneal shape data and refractive power data (which may be called data on distribution of refractive powers as well) including a correction pattern of the selected CL, the size of the optical zone, and both positions of and corrective diopters for the far and near vision zones each. FIG. 9 is an example of an input screen for the refractive power data shown on the display 21b. Data to be entered in each entry field on the right side of the display come with the selected CL. The data may be, for example, attached to a packing case and the like of the CL when the CL is manufactured, or the data may be furnished in a CL record book. This allows an operator to see the data and input them from the input control part 21c. Nevertheless, manual input is so troublesome and prone to invite a mistake that the following method may be practicable for input of the data.

Each of the packing cases and the like of a CL is provided with a record number for identification of CLs. The refractive power data on CLs associated with the record numbers of the CLs are stored beforehand in a database possessed in the computer 21. It may also be possible that the data on the CLs manufactured by a CL maker is stored in a CD-ROM to be incorporated into the computer 21 in advance. When the record number of the selected CL is entered in a CL Number entry field 70 shown in FIG. 9, the refractive power data concerning the CL may be retrieved from the database to be inputted. Alternatively, the refractive power data on the CLs may be stored in a bar-code form (or, as two-dimensional codes if the data come in large quantity), and may be then attached to the packing cases and the like of the CLs, so that the data may be read with a bar code reader to be inputted.

It should be noted that, if the trial use of the CL contributes to accurate diagnosis of refractive power data on a patient, the refractive power data on the CL are inputted, and then a value for a data item may be corrected as needed using the input control part 21c.

On the input screen shown in FIG. 9, a color map 75 of correction patterns is displayed graphically. The near and far vision zones are both expressed in color in accordance with the corrective diopters. An outer zone 76 on the color map 75 represents a transition zone. The graphic display of the color map 75 facilitates visible recognition of correction patterns and verification of the data inputted in correspondence with the CL selection.

Upon completion of inputting the pre-operative corneal shape data and the refractive power data, the main body of the computer 21a converts the refractive power data into the ablation data (data on distribution of ablation). Based on the ablation data, the control data for ablation are obtained according to the above-mentioned patterns, and are then transmitted to the control device 20. At the time of surgery, the operator observes the eye E through the observation optical system 17 to perform alignment of the beam directing optical system, and then inputs laser irradiation commencement signals to the control device 20 using a laser irradiation switch. The control device 20 controls the laser light source 1 and the driving units to irradiate a laser beam so that ablation may be carried out in any of the above-described manners.

Having fully been described, the present invention is intended to find correction data optimum for each patient so as to ensure precise correction made with a laser beam.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A correction data determining method of determining refractive correction data for a corneal refractive surgery apparatus with a laser beam causing ablation of corneal tissue of a patient's eye, comprising:

a process in which an ophthalmic examination of the patient's eye including a refractive power inspection is performed, and data on prescription provided to the patient's eye is obtained;

a process in which a first contact lens for providing the patient's eye with refractive power of a first correction pattern having a first far vision and near vision zone pattern, which corresponding to the obtained data on prescription is prepared, the first correction pattern of the first contact lens being created in association with correction patterns available with the corneal refractive surgery apparatus;

a process in which the first contact lens is put on the patient's eye for a trial use and a result of the trial use is checked to determine whether the result is good or bad; and a process in which, if the trial use of the first contact lens bears a good result, a corneal refractive correction pattern for the patient's eye is determined based on the first correction pattern of the first contact lens, and if the trial use of the first contact lens bears a bad result, a second contact lens for providing the patient's eye with refractive power of a second correction pattern having a second far vision and near vision zone pattern, which is different from the first correction pattern, is put on the patient's eye for a trial use, the second correction pattern of the second contact lens being created in association with the correction patterns available with the corneal refractive surgery apparatus, whereby the corneal refractive correction pattern for the patient's eye is determined based on a correction pattern of a contact lens of which a trial use bears a good result.

2. The correction data determining method according to claim 1, further comprising:

a process in which the determined corneal refractive correction pattern for the patient's eye or the correction pattern of the contact lens of which the trial use bears a good result is revised.

\* \* \* \* \*